(12) United States Patent
Sukhotnik et al.

(10) Patent No.: US 8,026,211 B2
(45) Date of Patent: Sep. 27, 2011

(54) METHODS AND FORMULATIONS FOR INCREASING INTESTINAL FUNCTION

(75) Inventors: Igor Sukhotnik, Haifa (IL); Naim Shehadeh, Kfar-Yassif (IL); Raanan Shamir, Herzlia (IL)

(73) Assignee: Technion Research & Development Foundation Ltd., Haifa (IL)

( * ) Notice: Subject to any disclaimer, the term of this patent is extended or adjusted under 35 U.S.C. 154(b) by 0 days.

(21) Appl. No.: 11/628,316

(22) PCT Filed: Jun. 2, 2005

(86) PCT No.: PCT/IL2005/000587
§ 371 (c)(1),
(2), (4) Date: Dec. 4, 2006

(87) PCT Pub. No.: WO2005/117951
PCT Pub. Date: Dec. 15, 2005

(65) Prior Publication Data
US 2007/0225211 A1 Sep. 27, 2007

Related U.S. Application Data

(60) Provisional application No. 60/575,803, filed on Jun. 2, 2004.

(51) Int. Cl.
*A61K 38/28* (2006.01)
*A61K 9/20* (2006.01)

(52) U.S. Cl. .................. 514/5.9; 424/464

(58) Field of Classification Search .................. None
See application file for complete search history.

(56) References Cited

U.S. PATENT DOCUMENTS

| 4,910,021 | A | 3/1990 | Davis et al. | |
|---|---|---|---|---|
| 7,429,564 | B2 * | 9/2008 | Arbit et al. | 514/4 |
| 2002/0064549 | A1 | 5/2002 | Shehadeh | |

OTHER PUBLICATIONS

Peacock et al. Impact of Insulin on Doxorubicin-induced Rat Host Toxicity and Tumor Regression. Cancer Res., 47, 4318-4322, 1987).*
Eizaguirre et al. "Effect of Growth Hormone, Epidermal Growth Factor, and Insulin on Bacterial Translocation in Experimental Short Bowel Syndrome", Journal of Pediatric Surgery, 35(5): 692-695, 2000. Abstract, Table 1.
Shehadeh et al. "Influence of Oral Insulin Supplementation on Carbohydrate, Lipid and Protein Metabolism in Weaned Balb/C Mice", Journal of Pedriatric Endocrinology & Metabolism, 16(3): 431-437, 2003. Abstract, P.436, 1-h Col., § 2.
Shulman "Effect of Enteral Administration of Insulin on Intestinal Development and Feeding Tolerance in Preterm Infants: A Pilot Study", Archives of Disease in Childhood. Fetal and Neonatal Edition, 86(2): F131-F133, 2002. Abstract, P.F131, 1-h Col., § 2, P.F133, 1-h Col.
Krauland et al. "Oral Insulin Delivery: The Potential of Thiolated Chitosan-Insulin Tablets on Non-Diabetic Rats", Journal of Controlled Release, 95(3): 547-555, 2004. Abstract.
Shamir et al. "Oral Insulin Supplementation Attenuates Atherosclerosis Progression in Apolipoprotein E-Deficient Mice", Atherosclerosis, Thrombosis & Vascular Biology, 23: 104-110, 2003.
Shehadeh et al. "Gastrointestinal Tract as a Target Organ for Orally Administrated Insulin", Journal of Pediatric Gastroenterology and Nutrition, 43: 276-281, 2006.
Skyler et al. "Effects of Oral Insulin in Relatives of Patients With Type 1 Diabetes. The Diabetes Prevention Trial-Type 1", Study Group, Diabetes Care, 28(5): 1068-1076, 2005.
Communication Pursuant to Article 94(3) EPC Dated Aug. 20,2009 From the European Patent Office Re.: Application No. 05747256.5.
Communication Pursuant to Article 96(2) EPC Dated Sep. 27, 2007 From the European Patent Office Re.: Application No. 05747256.5.
International Search Report Dated Oct. 7, 2005 From the International Searching Authority Re.: Application No. PCT/IL2005/000587.
Written Opinion Dated Oct. 7, 2005 From the International Searching Authority Re.: Application No. PCT/IL2005/000587.
Cefalu et al. "Inhaled Insulin: A Novel Route for Insulin Delivery", Expert Opinion on Investigational Drugs, 11(5): 687-691, May 2002. Abstract.
Heinemann et al. "Alternative Routes of Administration as An Approach to Improve Insulin Therapy: Update on Dermal, Oral, Nasal and Pulmonary Insulin Delivery", Current Pharmaceutical Design, 7(14): 1327-1351, Sep. 2001. Abstract.
Hoffman et al. "Pharmacokinetic Considerations of New Insulin Formulations and Routes of Administration", Clinical Pharmacokinetics, 33(4): 285-301, Oct. 1997. Abstract.
Siekmeier et al. "Inhaled Insulin—Does It Become Reality?", Journal of Physiology and Pharmacology, 59(6): 81-113, 2008.

* cited by examiner

*Primary Examiner* — Elly-Gerald Stoica
(74) *Attorney, Agent, or Firm* — Browdy and Neimark, PLLC

(57) ABSTRACT

A method for increasing intestinal function is provided. The method comprising orally and/or enterally administering to a subject in need thereof a therapeutically effective amount of insulin, thereby increasing intestinal function.

7 Claims, 9 Drawing Sheets

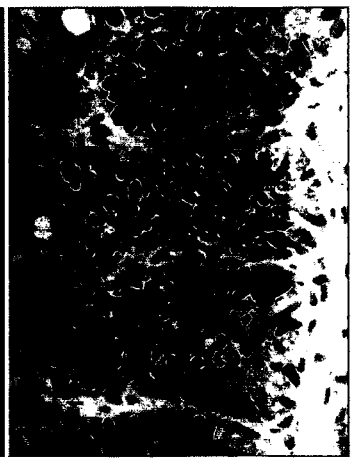

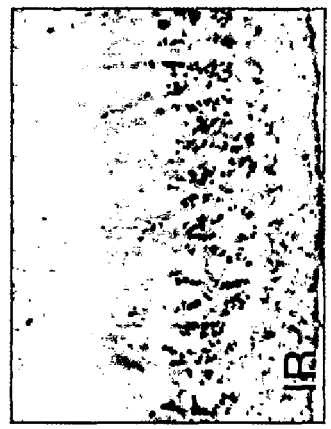

METHODS AND FORMULATIONS FOR INCREASING INTESTINAL FUNCTION

RELATED APPLICATIONS

This application is a National Phase of PCT Patent Application No. PCT/IL2005/000587 having International Filing Date of Jun. 2, 2005, which claims the benefit of U.S. Provisional Patent Application No. 60/575,803 filed on Jun. 2, 2004. The contents of the above Applications are all incorporated herein by reference.

FIELD AND BACKGROUND OF THE INVENTION

The present invention relates to methods and formulations for increasing intestinal function, which may be used for treating short bowel syndrome.

Short bowel syndrome (SBS) is defined as an intestinal failure following the loss of intestinal length or competence below the minimal amount necessary for the absorption of nutrients and a normal nutritional status [Sigalet D L. Short bowel syndrome in infants and children: an overview. Semin Pediatr Surg 2001; 10:49-55; Vanderhoof J A. Short bowel syndrome. Neonat Gastroenterol 1996; 23:377-86; Booth I W, Lander A D. Short bowel syndrome. Bailliere's Clin Gastroenterol 1998; 12:739-72].

SBS typically follows resection of 50% or more of the small intestine and is associated with diarrhea, steatorrhea, dehydration, electrolyte disturbances, malabsorption and progressive malnutrition [Vanderhoof J A. Short bowel syndrome. Neonat Gastroenterol 1996; 23:377-86; Booth I W, Lander A D. Short bowel syndrome. Bailliere's Clin Gastroenterol 1998; 12:739-72]. SBS is a common problem in pediatric surgery and occurs in newborns and infants suffering from necrotizing enterocolitis (NEC), intestinal atresia and volvulus requiring massive intestinal resection. In adults, Crohn's disease, radiation enteritis and massive resections due to catastrophic mesenteric vascular events, intestinal obstruction, and trauma represent the more common causes of SBS [DiBaise J K, Young R J, Vanderhoof J A. Intestinal rehabilitation and the short bowel syndrome. Am J Gastroenterol 2004; 99:1386-95]. SBS remains a significant cause of infant morbidity and mortality despite the availability of total parenteral nutrition (TPN), advances in resuscitation, availability of potent antibiotics, and modern techniques of organ support [Coran A G, Spivak D, Teitelbaum D H. An analysis of the morbidity and mortality of short bowel syndrome in the pediatric age group. Eur J Pediatr Surg 1999; 9:228-30].

The key to survival after massive small bowel resection is the ability of the residual intestine to adapt. In this setting, adaptation means progressive recovery from intestinal failure throughout which the small bowel increases its absorptive surface area and its functional capacity in an attempt to meet the body's metabolic and growth needs [O'Brien D P, Nelson L A, Huang F S, Warner B W. Intestinal adaptation: structure, function, and regulation. Semin Pediatr Surg 2001; 10:56-64]. Intestinal adaptation constitutes the best option for patients with SBS. In humans, intestinal adaptation begins within 24-48 hours of resection and includes morphologic (structural adaptation) and functional changes (functional adaptation) of the residual bowel. Structural adaptation includes increasing bowel diameter and length, villi elongation, deepening of the crypts, and increasing the rate of enterocyte proliferation, finally resulting in increased absorptive surface area and in increased numbers of enterocytes. Functional adaptation entails modifications of the brush border membrane permeability and up-regulation of carrier-mediated transport, ultimately resulting in increased nutrient absorption by isolated enterocytes. Although intestinal transplantation (IT) has emerged as a feasible alternative in the treatment of children with SBS during the last two decades, intestinal adaptation remains the only chance for survival in a subset of these patients. Considerable research over many years has focused on the identification of those trophic factors that may promote bowel absorption after massive intestinal resection and provide a successful outcome in patients with SBS. These factors include nutrients and other luminal constituents, gastrointestinal secretions, hormones and peptide growth factors [O'Brien D P, Nelson L A, Huang F S, Warner B W. Intestinal adaptation: structure, function, and regulation. Semin Pediatr Surg 2001; 10:56-64].

Another area in which there has been a considerable research effort over the last four decades is intestinal ischemia-reperfusion. Restoration of blood flow following intestinal ischemia is necessary to maintain cell function and viability; however, the reintroduction of oxygen can initiate a cascade of events that exacerbates intestinal tissue injury. The mechanisms of intestinal injury following ischemia-reperfusion event include nonspecific damage induced by ischemia per se and damage caused by reperfusion. Intestinal ischemia induces intestinal mucosal cell death, which is attributed mainly to a reduction of oxygen supply relative to metabolic demands, depletion of cellular energy stores and accumulation of toxic metabolites. The reperfusion phase may significantly exacerbate ischemia-induced mucosal injury via the formation of reactive oxygen species and reactive nitrogen species [Carden, D. L., Granger, D. N. J. Pathol., 2000, 190: 255; Granger, D. N., et al., Acta. Physiol. Scand. Suppl. 548: 47, 1986] and changes in lipid mediator synthesis [Tadros et al., Ann. Surg. 231: 566, 2000; Mangino et al., Cryobiology. 33: 404, 1996]. Additionally, an infiltration of intestinal wall by polymorphonuclear leucocytes and mast cells, which release the cytokines, growth factors, or other molecules leads to increased bowel permeability, gut barrier dysfunction, translocation of bacteria and bacterial products into the systemic circulation, causing multiple organ failure and death [Schoenberg et al., 1991, Gut, 32: 905; Yamamoto et al., 2001, J. Surj Research, 99:134].

Although necrosis is responsible for the intestinal cell death during the ischemic phase, apoptosis has recently been recognized to be a key phenomenon in enterocyte turnover and gut barrier function following IR insult [Noda et al., Am J Physiol, 1998, 274: G270]. Thus, reduction of apoptosis and stimulation of cell proliferation and differentiation following IR injury is a potential target for therapeutic intervention.

A number of nutrient substances have been evaluated in an attempt to maximize the adaptive response following IR injury and following resection of the small intestine. Diets high in glutamine, and high carbohydrate-low fat diets have been studied [Byrne, T. P., et al., 1995, Annals of Surgery 222(3):254-5; Scolapio, J. S. et al., 1997 Gastroenterology 113(4):1402-5; Sax, H., 1998, Journal of Parenteral and Enteral Nutrition 26(2):123-8].

Formulas containing amino acids have been studied in an attempt to avoid intact protein irritability and digestion [Bines, J. F. et al., 1998, Journal of Pediatric Gastroenterology & Nutrition 26(2):123-8]. Dietary restrictions of insoluble fiber, oxalates, and lactose have also been proposed [Lykins, T. S. et al., 1998, Journal of the American Dietetic Association 98(3):309-15] despite evidence that small amounts of lactose are tolerated [Marteau, P. M. et al., 1997, Nutrition 13(1):13-16]. Compositions comprising arachidonic acid and docosahexanoic acid have been proposed for improving the proliferative response during adaptation of the gastrointestinal tract for use in short bowel syndrome [U.S. Pat. Appl. 0010047036].

Hormones, such as growth hormone [Weiming et al., 2004, JPEN J Parenter Rectal-enteral Nutr. November-December; 28(6):377-81] and hormone related peptides (e.g., Glucagon-like peptide 2 and analogs thereof, U.S. Patent Application 0030162703) were shown to have a trophic effect on the intestine.

There is also a growing body of evidence suggesting that peptide growth factors may stimulate post-resection adaptive hyperplasia or improve intestinal recovery following intestinal ischemia. Peptide growth factors are divided into several families, including epidermal growth factor family, the transforming growth factor β family, the insulin-like growth factor (IGF) family, and the fibroblast growth factor family. In addition, a smaller number of peptide growth factors without structural similarities of the described families have also been identified and include hepatocyte growth factor and platelet-derived growth factor.

The insulin-like growth factor family includes three peptides: insulin, insulin-like growth factor I (IGF-I), and insulin-like growth factor II (IGF-II). Several experimental studies have suggested that both IGF-I and IGF-II are involved in to modulation of growth and differentiation of normal small bowel [Laburthe M. et al., 1988, Am J Physiol; 254: G457-G462] and following massive small bowel resection [Ziegler T R, Mantell M P, Chow J C et al. (1996) Gut adaptation and the insulin-like growth factor system: regulation by glutamine and IGF-1 administration. Am J Physiol 271: G866-875].

Lemmey and co-workers have demonstrated a positive effect of IGF-1 on body weight gain and intestinal absorptive function [Lemmey A B., et al., 1991, Am J. Physiol. February, 260(2 Pt 1):E213-9; Lemmey A B., et al., 1994, Growth Factors, 10(4):243-521 following bowel resection in a rat model. IGF-1 was shown to stimulate cell proliferation, increase villus height and promote nutrient absorptive capacity in an animal model of SBS [Olanrewaju H et al., 1992, Am J Physiol, 263: E282-286]. Ileal IGF-I mRNA expression in rats rose nearly twofold during intestinal adaptation after bowel resection, which was augmented with IGF-I administration [Ziegler et al., 1996, Am J Physiol, 271: G866-G875]. EGF and IGF-1 were shown to increase substrate absorption after small bowel resection in rats, and this increase in absorption persists after cessation of administration of these growth factors [Lukish et al., 1996, Gastroenterology, 110(Suppl): A818].

However, animal experiments and clinical trials using the above agents are at present inconclusive and there remains a widely recognized need for an intestinal tissue growth promoting agent which may be administered orally for the therapeutic treatment of various intestinal disorders, intestinal ischemic damage, impaired growth or loss of intestinal length.

The current advocacy of insulin therapy regimens involves subcutaneous injections and intravenous administration, since like other polypeptides, insulin is destroyed in the acidic environment of the stomach and by digestive enzymes of the pancreas and small intestine. Furthermore, insulin treatment is typically aimed at increasing the level of insulin in the blood (such as for insulin dependent diabetes), where the epithelial surface of the intestine itself presents an effective barrier to the absorption of insulin [Sukhotnik et al., 2002, J Surg Res. December; 108(2):235-42].

Accumulative evidence suggests a role of insulin in the growth and development of the small intestine. For example, insulin receptors are present on the luminal and basolateral membranes of enterocytes [Buts J P, De Keyser N, Marandi S, Maernoudt A S, Sokal E M, Rahier J, Hermans D. Expression of insulin receptors and of 60-kDa receptor substrate in rat mature and immature enterocytes. Am J Physiol Gastrointest Liver Physiol 273:G217-226, 1997)]. Additionally, insulin is present in human and pig colostrum and mature milk, substantiating its aforementioned potential role in small intestine growth and development.

Oral insulin was shown to possess a trophic effect on intestinal mucosa by stimulating ileal mass, mRNA and disaccharidase activity in the newborn miniature pig [Shulman et al., Pediatr Res. 1990 August; 28(2):171-512; Shulman R J, Tivey D R, Sunitha I, Dudley M A, Henning S J 1992. Effect of oral insulin on lactase activity, mRNA, and posttranscriptional processing in the newborn pig. J Pediatr Gastroenterol Nutr 14:166-172)]. In a recent clinical trial, the author has shown that enteral administration of insulin to preterm infants (26-29 weeks of gestational age) leads to a higher lactase activity and less feeding intolerance [Shulman R J, et al., Arch. Dis. Child. Fetal Neonatal Ed (2002); 88:F131-3].

Insulin was also shown to stimulate epithelial cell proliferation and differentiation of intestinal epithelial cells in vitro [Raj N. K. Sharma C. P., 2003, J Biomater Appl January 17(3):183-96]. Insulin accelerates enterocyte proliferation in the intestinal mucosa of suckling mice [Malone et al., Diabetes Res Clin Pract 2003 December; 62(3):187-95] and increases enzymatic activity of the dissacharidases [Buts J P, Duranton B, De Keyser N, Sokal E M, Maernhout A S, Raul F, Marandi S. Premature stimulation of rat sucrase-isomaltase (SI) by exogenous insulin and the analog B-Asp10 is regulated by a receptor-mediated signal triggering SI gene transcription. Pediatr Res 1998; 43:585-91]. Furthermore, insulin-receptor densities are selectively associated with intestinal mucosa growth in neonatal calves [Kojima H. 1998, Assoc Am Physicians, May-June; 110(3):197-206].

Moreover, Buts et al. had demonstrated preferential localization of insulin binding sites to the intestinal crypt cells, regardless of the age of the animal [Buts J P, De Keyser N, Marandi S, Maernoudt A S, Sokal E M, Rahier J, et al. Expression of insulin receptors and of 60-kDa receptor substrate in rat mature and immature enterocytes. Am J Physiol Gastrointest Liver Physiol (1997); 273:G217-261

Thus, prior art studies suggest that insulin is highly active in promoting lactase activity, mRNA levels and ileal mass when administered to healthy preterm infants or animal models, but does not suggest oral or enteral administration of insulin for increasing intestinal function in non-healthy infants.

The present inventors have previously shown that physiological concentrations (i.e., about 100 μu in maternal milk and 700 μu in colostrum) of insulin formulated in infant formula can be used for the manufacture of formulas which are similar to human milk. Such formulas are expected to protect new born babies from the development of Type-1 diabetes and to improve development and maturation of infants intestine (U.S. Pat. No. 6,399,090).

To date oral administration of insulin (not included in infant formulas) has not been suggested for improving intestinal function humans weaned of infant formula or non-human animal subjects.

SUMMARY OF THE INVENTION

According to one aspect of the present invention there is provided a method of increasing intestinal function comprising, orally and/or enterally administering to a subject in need thereof a therapeutically effective amount of insulin thereby increasing intestinal function.

According to still further features in the described preferred embodiment the subject suffers from intestinal malfunction or malnutrition.

According to still further features in the described preferred embodiment the subject suffers from a disease or a condition selected from the group consisting of short bowel syndrome, inflammation of the bowel, intestinal failure, chronic ulcerative colitis, Crohn's Disease, necrotizing enterocolitis, intestinal atresia, midgut volvulus, severe acute gastroenteritis, chronic gastroenteritis, cholera, chronic infections of the bowel, immunologic disorders affecting the small intestine, chemotherapy-associated intestinal malfunction, radiotherapy-associated intestinal malfunction, age associated weight loss, postgastrectomy syndrome, dumping syndrome, AIDS, diabetes, postvagotomy diarrhea, bariatric surgery-associated diarrhea, tube-feeding related diarrhea, parenteral feeding dependency, chronic secretory diarrhea, cancer, gastrointestinal peptide tumors, endocrine tumors, diarrhea associated with thyroid disorders, diarrhea due to bacterial overgrowth, chronic diarrhea in gastrinoma, acute diarrhea, chronic diarrhea, infectious diarrhea, antibiotic-associated diarrhea, irritable bowel syndrome, chronic diarrhea associated with maldigestion and malabsorption, chronic diarrhea in idiopathic primary gastrointestinal motility disorders, chronic diarrhea associated with collagenous colitis, nutritional deficiency, anemia, cystic fibrosis, and an eating disorder, ischemia reperfusion and sepsis.

According to still further features in the described preferred embodiment the subject is a human subject.

According to still further features in the described preferred embodiment the subject is a non-human mammal.

According to still further features in the described preferred embodiment the subject is an infant.

According to still further features in the described preferred embodiment the orally administering is effected by an oral dosage unit.

According to still further features in the described preferred embodiment the oral dosage unit comprises from about 1 mu to about 10,000 units of the insulin.

According to still further features in the described preferred embodiment the insulin is administered in a amount ranging from about 1 mu/Kg body weight/day to about 100 u/Kg/day.

According to still further features in the described preferred embodiment the insulin has an amino acid sequence of human insulin or functional equivalents thereof.

According to still further features in the described preferred embodiment the insulin is recombinant insulin.

According to still further features in the described preferred embodiment the insulin is synthetic insulin.

According to still further features in the described preferred embodiment the insulin is a purified natural insulin.

According to another aspect of the present invention there is provided an oral dosage unit form comprising from about 1 mu to about 10,000 units of insulin.

According to still further features in the described preferred embodiment the oral dosage unit form is solid.

According to still further features in the described preferred embodiment the oral dosage unit is selected from the group consisting of a pill, a dragee, a tablet and a capsule.

According to still further features in the described preferred embodiment the oral dosage unit further comprising a pharmacological agent.

According to yet another aspect of the present invention there is provided a method of increasing intestinal function of a pharmacological agent, the method comprising orally and/or rectal-enterally administering to a subject in need thereof a therapeutically effective amount of insulin prior to, concomitant with or following administration of the pharmacological agent, thereby increasing intestinal absorption of the pharmacological agent.

According to still further features in the described preferred embodiment each of the insulin and the pharmacological agent are formulated in a dosage unit.

According to still further features in the described preferred embodiment the insulin and the pharmacological agent are formulated in a dosage unit.

According to still further features in the described preferred embodiment the dosage unit is for oral administration.

According to still another aspect of the present invention there is provided use of insulin for the manufacture of a medicament for increasing intestinal function.

According to still further features in the described preferred embodiment the insulin is formulated for oral or enteral administration.

The present invention successfully addresses the shortcomings of the presently known configurations by providing methods and formulations for increasing intestinal function.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and to readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3a-c are photographs depicting the effect of bowel resection and oral insulin on enterocyte proliferation. These representative sections demonstrate that cell proliferation is increased following bowel resection (SBB) compared to sham animals (Sham). Following administration of oral insulin, SBS-rats (SBS-INS) demonstrated a marked increase in a number of proliferating cells compared to SBS-nontreated animals.

FIGS. 9a-c are photographs depicting the effect of IR and oral insulin on enterocyte proliferation. These representative sections demonstrate that cell proliferation is decreased following IR compared to sham animals. Following administration of oral insulin, IR-rats demonstrated a marked increase in a number of proliferating cells compared to IR-nontreated animals.

DESCRIPTION OF THE PREFERRED EMBODIMENTS

Figure 1:
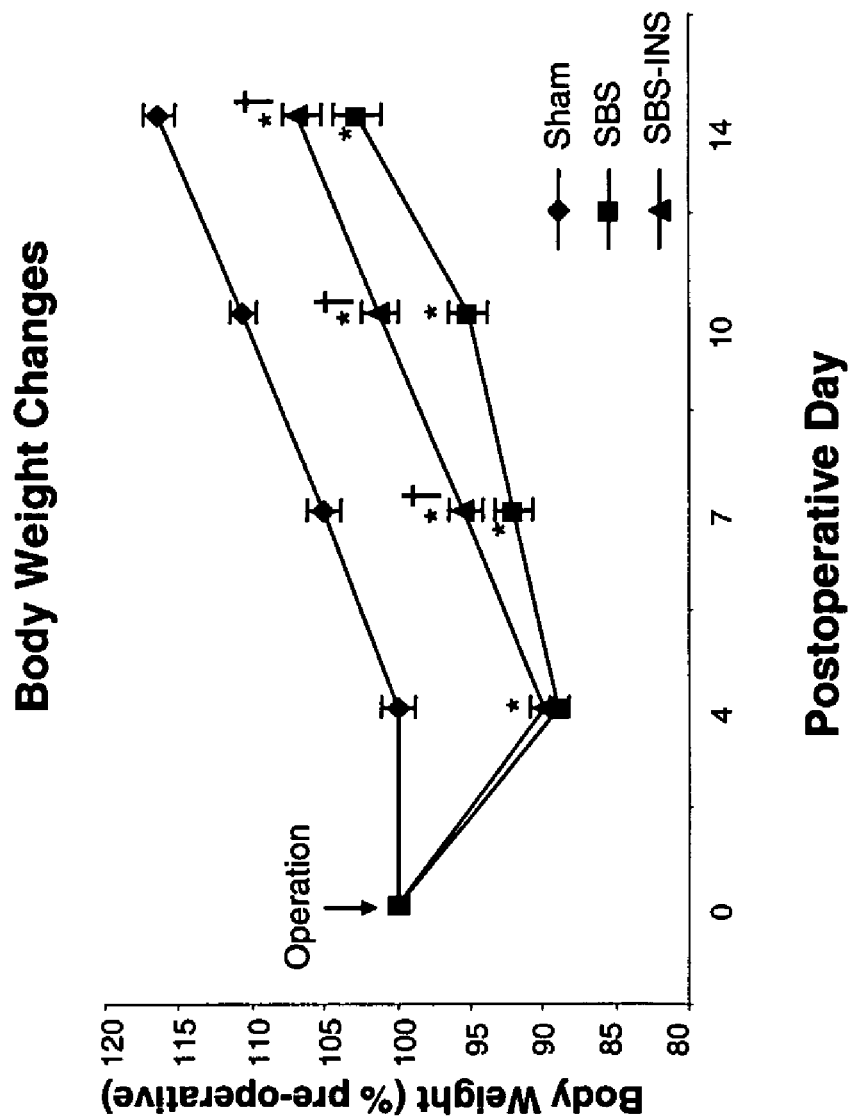
FIG. 1 is a graph depicting body weight changes expressed as % of preoperative weight (mean±SEM) in control (Sham) and resected rats untreated (SBS) or treated with oral insulin. SBS—short bowel syndrome rats; INS—insulin, * $p<0.05$ SBS vs Sham rats, † $p<0.05$ SBS-INS vs SBS rats.

The present invention is of formulations and methods for increasing intestinal function which can be used for diseases or conditions associated with intestinal malfunction.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The etiology of inadequate intestinal function includes intestinal loss due to development abnormalities such as intestinal atresia and in utero midgut volvus; postnatal loss from surgical resection after infarction (e.g., midgut volvulus or vascular occlusion), trauma or tumor; inflammation, such as is due to infection (e.g., necrotizing enterocolitis and acute gastroenteritis) and autoimmune etiologies such as in Crohn's Disease and ulcerative colitis.

To date, there is no effective treatment and current management includes total parenteral nutrition, which itself is a source of significant morbidity and mortality.

Accumulative evidence suggests a role for insulin in the proliferation and differentiation of intestinal epithelial cells vitro [Raj N. K. Sharma C. P., 2003, J Biomater Appl January 17(3):183-96].

The present inventors have previously shown that insulin formulated in infant formula can be used for the manufacture of formulas which are similar to human milk. Such formulas are expected to protect new born babies from the development of Type-1 diabetes and to improve development and maturation of infants intestine (U.S. Pat. No. 6,399,090).

To date oral or enteral administration of insulin (not included in infant formulas) has not been suggested for improving intestinal function and/or treating or preventing conditions associated with intestinal malfunction (e.g., intestinal failure) in humans (e.g., weaned of infant formula) or non-human animal subjects.

While reducing the present invention to practice, the present inventors uncovered that oral administration of insulin can be used to improve intestinal function.

As is illustrated hereinbelow and in the Examples section which follows, oral insulin administration to a rat model of short bowel syndrome (SBS) caused dramatic adaptive gut growth (see Example 1). These findings were substantiated in human infants suffering from SBS, where oral administration of insulin reduced stool output, decreased jaundice, increased the amount of oral feeds and reduced the need for parenteral feeding (Example 2). Finally, oral insulin accelerated intestinal recovery, enhanced enterocyte proliferation and decreased cell death via apoptosis following ischemia-reperfusion event.

Thus, according to one aspect of the present invention there is provided a method of increasing intestinal function.

As used herein the phrase "increasing intestinal function" refers to increasing at least one intestinal activity associated with the heterogenic cellular environment of the intestine (e.g., small intestine). Examples of intestinal activities include, but are not limited to, absorption (the transport of a substance from the intestinal lumen through the barrier of the mucosal epithelial cells into the blood and/or lymphatic systems e.g., nutrient absorption), digestion, motility, adaptation (described in length in the Background section), immunological function (e.g., antigen recognition) and barrier function.

The method according to this aspect of the present invention is effected by orally and/or enterally administering to a subject in need thereof a therapeutically effective amount of insulin, thereby increasing intestinal function of the subject.

As used herein the term "insulin" refers to the hormone produced by the pancreas which is typically necessary for glucose to be able to enter the cells of the body and be used for energy (see U.S. Pat. No. 6,399,090). Insulin of the present invention refers also to functional equivalents of insulin, such as fragments thereof displaying insulin activity and functional peptide-mimetics thereof.

As used herein the term "functional" refers to the ability to increase intestinal function.

As used herein the term "mimetics" when made in reference to peptides refers to molecular structures, which serve as substitutes for the insulin of the present invention in increasing intestinal function (Morgan et al. (1989) Ann. Reports Med. Chem. 24:243-252 for a review of peptide mimetics). Peptide mimetics, as used herein, include synthetic structures (known and yet unknown), which may or may not contain amino acids and/or peptide bonds, but retain the structural and functional features of insulin. The term, "peptide mimetics" also includes peptoids and oligopeptides, which are peptides or oligomers of N-substituted amino acids [Simon et al. (1972) Proc. Natl. Acad. Sci. USA 89:9367-9371]. Further included as peptide mimetics are peptide libraries, which are collections of peptides designed to be of a given amino acid length and representing all conceivable sequences of amino acids corresponding thereto. Methods for the production of peptide mimetics are described hereinbelow.

According to a preferred embodiment of the present invention, insulin is selected from the following insulin types: recombinant insulin, synthetic insulin or active fragments or functional mimetics thereof, purified natural insulin, and insulin having an amino acid sequence of human insulin (e.g., human insulin). Some of these types are overlapping and therefore the insulin of choice may be categorized to more to than a single type of the types listed. Human recombinant insulin is available in a pure form from Eli Lilly & Co, USA. Human natural purified insulin is available in a pure form from Novo Nordisk, Denmark. Crude extracts may also be useful, depending on the method of their manufacturing. Synthetic insulin may be manufactured using commercially available building units for solid-phase peptide synthesis, as well known in the art.

As used herein the phrase "enteral administration" refers to administration of a pharmacological agent through any part of the gastro-intestinal tract, such as rectal administration, colonic administration, intestinal administration (proximal or distal) and gastric administration.

As used herein the phrase "subject in need thereof" refers to a mammal of any age (e.g., infant such as term or preterm infant, adult or old) or sex, preferably a human, which can benefit from increased intestinal function. Examples of non-human mammals include domestic animals such as cats, dogs, cattle, sheep, pigs, goats, poultry and equines.

According to one embodiment of this aspect of the present invention the subject is a non-healthy subject, which suffers from intestinal malfunction (i.e., reduced function as compared to intestinal function of a healthy subject of the same age, or even complete intestinal failure) such as caused by a disease or condition associated with inadequate intestinal function such as due to reduced intestinal absorptive, anti-inflammatory, barrier, digestive and/or motility functions and/or reduced tissue mass; and/or malnutrition such as due to eating disorders, chemotherapy or radio-therapy and the like.

For example, inadequate intestinal function can be due to developmental abnormalities such as, intestinal atresia; in utero midgut volvulus; postnatal loss from surgical resection such as due to infarction (e.g., midgut volvulus or vascular occlusion) trauma; ischemia (e.g., ischemia reperfusion) or tumor; or inflammation such as caused by infection (i) necrotizing enterocolitis (ii) acute gastroenteritis (e.g., cholera) or autoimmune causes (i) Crohn's Disease (ii) ulcerative colitis.

Examples of diseases and conditions which are associated with intestinal malfunction or malnutrition include, short bowel syndrome, inflammation of the bowel, intestinal failure, chronic ulcerative colitis, Crohn's Disease, necrotizing enterocolitis, intestinal atresia, midgut volvulus, severe acute gastroenteritis, chronic gastroenteritis, cholera, chronic infections of the bowel, immunologic disorders affecting the small intestine, chemotherapy-associated intestinal malfunction, radiotherapy-associated intestinal malfunction, age associated weight loss, postgastrectomy syndrome, dumping syndrome, AIDS, diabetes, postvagotomy diarrhea, bariatric surgery-associated diarrhea, tube-feeding related diarrhea, parenteral feeding dependency, chronic secretory diarrhea, cancer, gastrointestinal peptide tumors, endocrine tumors, diarrhea associated with thyroid disorders, diarrhea due to bacterial overgrowth, chronic diarrhea in gastrinoma, acute diarrhea, chronic diarrhea, infectious diarrhea, antibiotic-associated diarrhea, irritable bowel syndrome, chronic diarrhea associated with maldigestion and malabsorption, chronic diarrhea in idiopathic primary gastrointestinal motility disorders, chronic diarrhea associated with collagenous colitis, nutritional deficiency, anemia, cystic fibrosis, liver disease, an allergy, and an eating disorder (e.g., anorexia, bulimia), injury, ischemia reperfusion and sepsis.

"Merck's Veterinary Manual" provides a detailed description of animal's intestinal disorders, which can be treated according to this aspect of the present invention.

As mentioned, the teachings of the present invention can be used for treating the above described diseases or conditions.

As used herein the term "treating" refers to preventing, curing, reversing, attenuating, alleviating, minimizing, suppressing or halting the deleterious effects of a condition or disorder associated with abnormal intestinal function symptoms and/or disease state, as described hereinabove.

According to another embodiment of this aspect of the present invention the subject can be a healthy subject, in which case increasing intestinal function is effected to gain weight such as for commercial reasons (such as in livestock e.g., farm animals or poultry) or for prophylactic reasons, such as prior to anti-cancer therapy, in which case the subject is expected to loose weight. Alternatively, increasing intestinal function may be beneficial for athletes, travelers or in combat to avoid weight loss.

Insulin of the present invention is formulated in a pharmaceutical composition or veterinary formulation for oral or enteral (e.g., rectal) administration.

As used herein, a "pharmaceutical composition" refers to a preparation of one or more of the active ingredients (e.g., insulin) described herein with other chemical components such as physiologically suitable carriers and excipients. The purpose of a pharmaceutical composition is to facilitate administration of a compound to an organism.

As used herein, the term "active ingredient" refers to the insulin accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

It will be appreciated that insulin of the present invention may be released in a any portion of the gastro-intestinal tract, as peptide digestion fragments of insulin may exert the desired activity in the intestine (i.e., increased intestinal function).

According to a presently known configuration of the present invention insulin is released in the intestine. Typically, to achieve successful intestinal delivery, a drug needs to be protected from absorption and/or the environment of the upper gastrointestinal tract (GIT) and then be abruptly released into the proximal intestine, which is considered the optimum site for intestine-targeted delivery of drugs. Various strategies for targeting orally administered drugs to the intestine include covalent linkage of a drug with a carrier, coating with pH-sensitive polymers, formulation of timed released systems, exploitation of carriers that are degraded specifically by intestineic bacteria, bioadhesive systems and osmotic controlled drug delivery systems. Various prodrugs (sulfasalazine, ipsalazine, balsalazine and olsalazine) have been developed that are aimed to deliver 5-amino salicylic acid (5-ASA) for localized chemotherapy of inflammatory bowel disease (IBD). Microbially degradable polymers especially azo crosslinked polymers have been investigated for use in targeting of drugs to intestine. Certain plant polysaccharides such as amylose, inulin, pectin and guar gum remains unaffected in the presence of gastrointestinal enzymes and pave the way for the formulation of intestine targeted drug delivery systems. The concept of using pH as a rigger to release a drug in the intestine is based on the pH conditions that vary continuously down the gastrointestinal tract. Times dependent drug delivery systems have been developed that are based on the principle to prevent release of drug until 3-4 h after leaving the stomach. Redox sensitive polymers and bioadhesive systems have also been exploited to deliver the drugs into the intestine.

Colonic release is expected to reduce inflammatory reactions and increase motility, according to the present invention.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Oral administration is preferred for administration to pre-term infants.

Pharmacological preparations for oral use according to the present invention are preferably produced using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

Insulin of the present invention can be formulated in a solid dosage unit such as for oral administration or rectal administration (as described below). Such a dosage unit form can include, for example 1 mu (munit)-10,000 u (unit) of insulin (where 100 u=3.5 mg), preferably 1 mu (munit)-1000 u (unit) of insulin, preferably 1 mu-500 u of insulin, 1 mu-200 u of insulin, preferably 1 mu-100 u of insulin, preferably 1 mu-10 u of insulin The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., insulin) effective to prevent, alleviate, or ameliorate symptoms of a disorder (e.g., ischemia) or prolong the survival of the subject being treated.

As used herein in the specification and claims section that follows, the phrase "therapeutically effective amount" refers to an amount which is sufficient to improve intestinal function. The "therapeutically effective amount" can be assessed by growth in infants and children and by body weight in adults, by stool output, assessment of nutrient of interest (e.g., Fe, Zinc, potassium, etc.), patients general well being or alternatively in-vitro (e.g., biopsies exemplified in the Examples section which follows.

The "therapeutically effective amount" will, of course, be dependent on, but not limited to the subject being treated, the severity of the anticipated affliction, the manner of administration, as discussed herein and the judgment of the prescribing physician. [See e.g. Fingl, et al., (1975) "The Pharmacological Basis of Therapeutics", Ch. 1 p. 1].

Determination of a therapeutically effective amount is well within the capability of those skilled in the art.

For any preparation used in the methods of the invention, the therapeutically effective amount or dose can be estimated initially from in vitro assays. For example, a dose can be formulated in animal models (e.g. Example 1—Rat model for SBS) such information can be used to more accurately determine useful doses in humans.

Preferably, insulin is administered in an amount ranging from 1 mu/Kg body weight/day to about 100 u/Kg/day, where 100 u=3.5 mg. The effective dosage will be determined according to the age of the subject, the severity of the disease and the purpose of treating (i.e., prophylactic or therapeutic).

Toxicity and therapeutic efficacy of the active ingredients described herein can be determined by standard pharmaceutical procedures in vitro, in cell cultures or experimental animals. The data obtained from these in vitro and cell culture assays to and animal studies can be used in formulating a range of dosage for use in human.

Depending on the severity and responsiveness of the condition to be treated, dosing can be effected over a short period of time (i.e. several days to several weeks) or until cure is effected or diminution of the disease state is achieved.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

The small intestine is also an important site for the absorption of pharmacological agents. The proximal part of the small intestine has the greatest capacity for absorption of drugs. Intestinal absorption of drugs is influenced to a great extent by many of the same basic factors that affect the digestion and absorption of nutrients, water and electrolytes. It is thus suggested, that the teachings of the present invention can also be used for increasing intestinal absorption of a pharmacological agent, where insulin serves essentially as a carrier for increasing bioavailability of the pharmacological agent.

Thus, according to another aspect of the present invention there is provided a method of increasing intestinal absorption of a pharmacological agent.

The method of this aspect of the present invention is effected by orally and/or rectal-enterally administering to a subject in need thereof a therapeutically effective amount of insulin prior to, concomitant with or following administration of the pharmacological agent, thereby increasing intestinal absorption of the pharmacological agent.

As used herein the phrase "pharmacological agent" refers to a medical drug.

It will be appreciated that each of the insulin and the pharmacological agent can be formulated in a dosage unit.

Alternatively, the insulin and the pharmacological agent can formulated together in a single dosage unit.

Examples of pharmacological agents which can be co-administered with the insulin of the present invention include, but are not limited to, antibiotics, chemotherapy, anti-diarrheal and anti-inflammatory drugs. Growth factors such as Hepatocyte Growth Factor (HGF), epidermal growth factor (EGF), Interleukin-11 (IL-11), glucagon-like peptide (GLP-2), and insulin-like growth factors such as insulin-like growth factor-1 (IGF-1) may also be included with the administration of insulin or provided separately.

It will be appreciated that nutritional supplements, may be administered as well with an effective dose of insulin. Nutritional supplements or nutrients may include rectal-enteral formulas and glutamine. The nutritional supplements may be administered along with the insulin or alternatively the nutritional supplements may be provided separately by the same or different administration routes Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Oral Insulin Supplementation in a Rat Model of SBS

Methods

Animal treatment: Animals were obtained from the Rappaport Faculty of Medicine (Technion, Haifa, Israel). Male rats weighing 240-260 g were kept in individual stainless steel cages at constant temperature and humidity, and a 12-hour light-dark cycle was maintained. Rats were fasted 12 hours prior to the experiment with free access to water. Animals underwent one of two surgical procedures: bowel transection and re-anastomosis or 75% bowel resection and anastomosis. General anesthesia was induced with Pentobarbital (IP 40 mg/kg). Using sterile techniques, the abdomen was opened using a midline incision. In sham rats, simple bowel transection and end-to-end re-anastomosis was performed 15 cm proximal to ileo-cecal junction. In SBS animals, small bowel was resected from a point 5 cm distal to the ligament of Treitz to a point 10 cm proximal to the ileo-cecal junction. Bowel continuity was restored by end-to-end anastomosis using 5-0 Vicryl interrupted sutures. For all operations, the abdominal cavity was closed in two layers with a running suture of 3-0 Dexon. Prior to closure of the abdomen, the rats were resuscitated with a 3 ml intraperitoneal injection of warm normal saline. Rats were fasted for 24 hours but were allowed free access to water.

Experimental design: Forty rats were randomly assigned to one of three groups:

Group A—sham-rats underwent bowel transection (sham, n=14) and than fed with regular chow diet.

Group B—SBS-animals underwent bowel resection (SBS, n=13) and than fed regular chow diet.

Group C—SBS-Insulin (SBS-INS, n=13) rats underwent bowel resection and were fed regular chow diet and water containing insulin (ACTRAPID insulin, NOVO NORDISK, Denmark) at concentration of 1 u/ml. Food and fluid intake of animals were monitored as well as weight for a period of 14 days following treatment after which the animals were sacrificed following intraperitoneal injection of pentobarbital (75 mg/kg).

Intestinal adaptation parameters: The small bowel was rapidly removed, rinsed with cold isotonic saline and divided into two segments: jejunum proximal to anastomosis and terminal ileum. Each segment was weighed, cut longitudinally, bowel circumference was measured in three equidistant points as described by Dowling [Dowling R H, Booth C C, 1967, Clin Sci; 32: 139-149] and the mean circumference was calculated. Mucosa was scraped using a glass slide, collected and weighed. Bowel and mucosal weight was calculated per cm of bowel length per 100 g of body weight as described previously [Sukhotnik I, et al., 2002, J Surg Res., December; 108(2):235-42]. Although bowel length may change due to spasm or bowel distension, the calculation per unit of bowel length is considered to be the gold standard in describing structural changes in intestine. DNA and protein were extracted using TRIzol reagent (Rhenium LTD, Jerusalem). The DNA concentrations were recorded in a spectrophotometer and calculated per cm of bowel length. Final protein concentration was measured spectrophotometrically using a commercially available kit (Bio-Rad, Protein Assay) and was calculated per cm of bowel length.

Histology: Histological sections were prepared from the proximal jejunum and distal ileum and from comparable sites in control animals. Segments of small bowel were fixed for 24 hours in 10% formalin and processed into standard paraffin blocks. Five-micron tissue slices stained with hematoxylin-eosin. The sections were studied microscopically using a micrometer eyepiece. Histological images were loaded on a 760×570 pixels resolution buffer using a computerized image analysis system composed of a trichip RGB video-camera (Sony, Japan), installed on a light microscope (Zeiss, Germany) and attached to an IBM compatible personal computer (Pentium III, MMX, 450 mhz, 125 MB RAM), equipped with a frame grabber. Images were captured, digitized and displayed on a high resolution color 17 inch monitor. The villus height and crypt depth were measured using the Image Pro Plus 4 image analysis software (Media Cybernetics, Baltimore, Md., USA). Ten villi and crypts in each section were measured and the mean reading was recorded in microns.

Crypt Cell Proliferation and Enterocyte Apoptosis: Rats were injected with standard 5-bromodeoxyuridine (5-BrdU) labeling reagent (Zymed Lab, Inc, CA) at dose 1 ml per 100 g body weight two hours prior to sacrifice. Tissue slices (5 µm) were deparaffinized with xylene, rehydrated with graded alcohol, and stained with a biotinylated monoclonal anti-BrdU antibody system using BrdU Staining Kit (Zymed Lab, Inc, CA). An index of proliferation was determined as the ratio of crypt cells staining positively for BrdU per 10 crypts.

Apoptosis of enterocytes was assessed by terminal deoxyuridine nick-end labeling (TUNEL) immunohistochemical assay using the I.S. Cell Death Detection kit (Boehringer Mannheim GmbH, Mannheim, Germany). 5 µm thick paraffin-embedded sections were deparaffinized, rehydrated in graded alcohol, and microwave-pretreated in 10 mM citrate buffer (pH 6.0) for 10 minutes. After washing in phosphate-buffered saline (PBS), the specimens were incubated in buffer containing a nucleotide mixture with fluorescein-labeled deoxy-UTP and TdT (Boehringer Mannheim GmbH, Mannheim, Germany) at 37° C. for 1 h. Following washing, the slides were incubated with blocking solution (3% $H_2O_2$ in methanol) for 10 minutes and were stained with anti-fluorescein antibody, Fab fragment from sheep, conjugated with horse-radish peroxidase (converter—POD) at 37° C. for 30 minutes. AES substrate (Zymed Laboratories) was applied for color development. For each group, the number of stained cells was counted in at ten villi in areas without necrosis. The apoptotic index (AI) was defined as the number of apoptotic TUNEL-positive cells per ten villi. All measurements were performed by a qualified pathologist blinded as to the source of intestinal tissue.

Statistical analysis: The data are expressed as the mean±SEM. A paired Student's t-test and the non-parametric Kruskal-Wallis ANOVA test were used as indicted. $p<0.05$ was considered statistically significant.

Results

Body weight: The sham-operated control rats (Group A) maintained constant body weight for the four first post-operative days followed by a gradual increase in weight throughout the two-week's observation period. Resected rats (Groups B and C) demonstrated a significantly lower body weight from day 4 through 14 following operation compared to their sham-operated counterparts. SBS-INS rats (Group C)

gained weight at greater rate from day 7 through 14 compared to SBS-nontreated animals (Group B) (p<0.05).

Macroscopic bowel appearance: Two weeks following bowel resection, there was an increase in intestinal thickness and diameter. Compared to sham animals (Group A), SBS-rats (Group B) showed a significantly greater bowel circumference in jejunum and ileum. Exposure to oral insulin resulted in additional bowel enlargement. SBS-insulin rats (Group C) demonstrated an additional increase in jejunal and ileal bowel circumference compared to SBS-untreated animals (Group B).

Overall mean bowel weight rose significantly in jejunum (four fold increase, p<0.05) and in ileum (two fold increase, p<0.05) in SBS-rats (group B) compared to sham animals (group A). Following oral insulin administration, (Group C) SBS rats demonstrated an additional significant increase in jejunal (18%, p<0.05) and ileal (40%, p<0.05) overall weight compared to SBS-untreated animals.

Changes in mucosal weights were similar to those of bowel weights. SBS-rats (Group B) demonstrated a three fold increase in jejunal mucosal weight (p<0.05) and a two fold increase in ileal mucosal weight (p<0.05) compared to sham animals (Group A). Oral insulin supplemented group (Group C) demonstrated an additional 33% increase in jejunal mucosal weight (p<0.05) and an almost two fold increase in ileal mucosal weight (p<0.05) compared to SBS-untreated counterparts.

Mucosal DNA and protein: Adaptation in residual bowel in the resected group (Group B) was manifested by a 2.7-fold increase in jejunal (p<0.05) and a 1.6-fold increase in ileal (p<0.05) DNA content compared to sham animals. Oral insulin supplementation resulted in an almost two-fold increase in ileal DNA content compared to SBS untreated animals (p<0.05).

Mucosal protein content increased significantly following bowel resection in both jejunum (three-fold increase, p<0.05) and ileum (1.4-fold increase, p<0.05). Oral insulin administration (Group C) induced an additional two-fold increase in ileal (p<0.05) mucosal protein content compared to SBS-untreated animals (Group B).

Microscopic bowel appearance: SBS-rats (Group B) showed a marked increase in villus height in jejunum (785±34 vs 529±34 μm, p<0.05) and ileum (672±24 vs 462±32 μm, p<0.05) and crypt depth in jejunum (209±15 vs 163±9 μm, p<0.05) and ileum (172±11 vs 147±7 μm, p<0.05) compared to Sham animals (Group A). SBS-insulin rats (Group C) demonstrated a 15% increase in ileal villus height (p<0.05), a 15% increase in jejunal (p<0.05) and 40% increase in ileal (p<0.05) crypt depth compared to SBS-untreated animals (Group B).

Enterocytes proliferation and apoptosis: Bowel resection (Group B) resulted in a significant increase in enterocyte proliferation index in jejunum (258±17 vs 154±7 BrdU positive cells/10 crypts, p<0.05) and ileum (263±15 vs 182±9 BrdU positive cells/10 crypts, p<0.05) compared to sham animals. Oral insulin administration (Group C) induced an additional 36% increase in proliferation index in jejunum (p<0.05) and a 52% increase in proliferation index in ileum (p<0.05) compared to SBS-untreated animals (Group B).

Significantly greater numbers of apoptotic cells appeared in the villi of jejunum (29±7 vs 13±4 TUNEL positive cells/10 villi, p<0.05) and ileum (33±8 vs 14±5 TUNEL positive cells/10 villi, p<0.05) in SBS rats (Group B) compared to sham animals. Exposure to oral insulin led to a significant decrease in the apoptotic index in jejunum (11±3 vs 29±7 TUNEL positive cells/10 villi, p<0.05) and did not affect apoptotic cells number in ileum compared to SBS-untreated animals (Group B).

Conclusion

Oral insulin supplementation dramatically enhanced structural intestinal adaptation. Overall bowel and mucosal weight also increased with a synergistic increase in bowel circumference. However, an approximately 10% increase in bowel diameter was accompanied with a 20-50% increase in overall bowel weight and a 30-200% increase in mucosal weight in the remaining segments (see FIG. 1). These data support the concept that mucosal hyperplasia rather than bowel enlargement is responsible for increased bowel and mucosal weights calculated per cm of bowel length.

Oral insulin significantly increased ileal mucosal DNA and protein. Parallel increases in mucosal DNA and protein indicate that the greater ileal mass of animals treated with oral insulin can be attributed to cellular hyperplasia. Because the DNA and protein content is directly proportional to mucosal cell number, these measurements exclude such factors as edema or vascular engorgement as responsible for differences in mucosal mass.

FIG. 2a and FIGS. 3a-c show an increase in the mucosal proliferation of functioning intestine, as demonstrated by an increased cell proliferation index following oral insulin administration, suggests an activated enterocyte turnover and may be considered as a main mechanism of mucosal hyperplasia in the residual bowel. Increased villus height and crypt depth are the result of increased proliferation and accelerated migration along the villus, and are a marker for the increased absorptive surface area. Most significant differences were observed in terminal ileum, since hyperplasia in proximal jejunum was less prominent. Following bowel resection, partial obstructive effects may explain the small bowel enlargement in the jejunum. However, the significant increase in mucosal parameters in the remnant of ileum must be considered an indirect measure of true structural intestinal adaptation.

Although bowel and mucosal weight increased significantly in the jejunum, this change was not associated with an increase in mucosal DNA, mucosal protein or villi height in this segment. However, a marked increase in ileal bowel and mucosal weight was accompanied by a two-fold increase in mucosal DNA and protein in this area, a 15% increase in villi height and a 40% increase in crypt depth compared to SBS-untreated animals, suggesting active proliferating process.

Figure 2B:
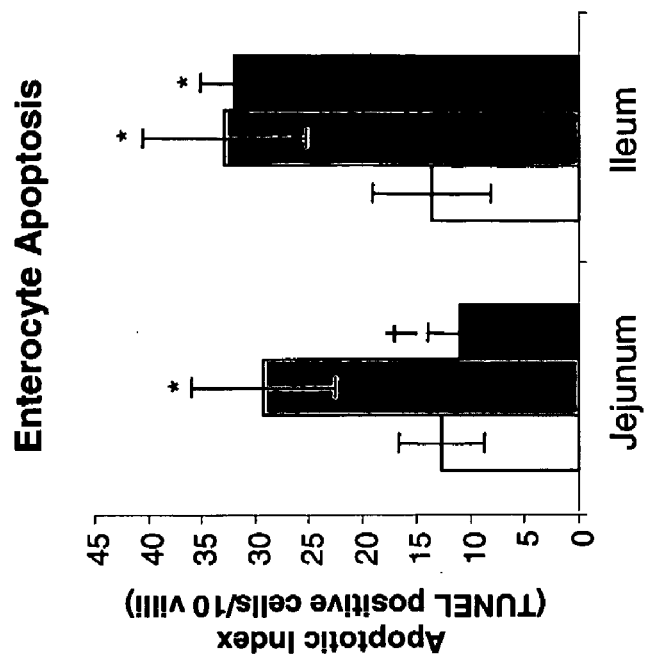
FIGS. 2a-b are graphs depicting the effect of bowel resection and oral insulin on crypt cell proliferation (FIG. 2a) and enterocyte apoptosis (FIG. 2b) in jejunum and ileum (mean±SEM). 5-BrdU incorporation into proliferating jejunal and ileal crypt cells was detected with a goat anti-BrdU antibody and TUNEL assay was used to determine enterocytes apoptosis. SBS—short bowel syndrome rats; INS—insulin, * p<0.05 SBS vs Sham rats, † p<0.05 SBS-INS vs SBS rats.
Figure 2A:
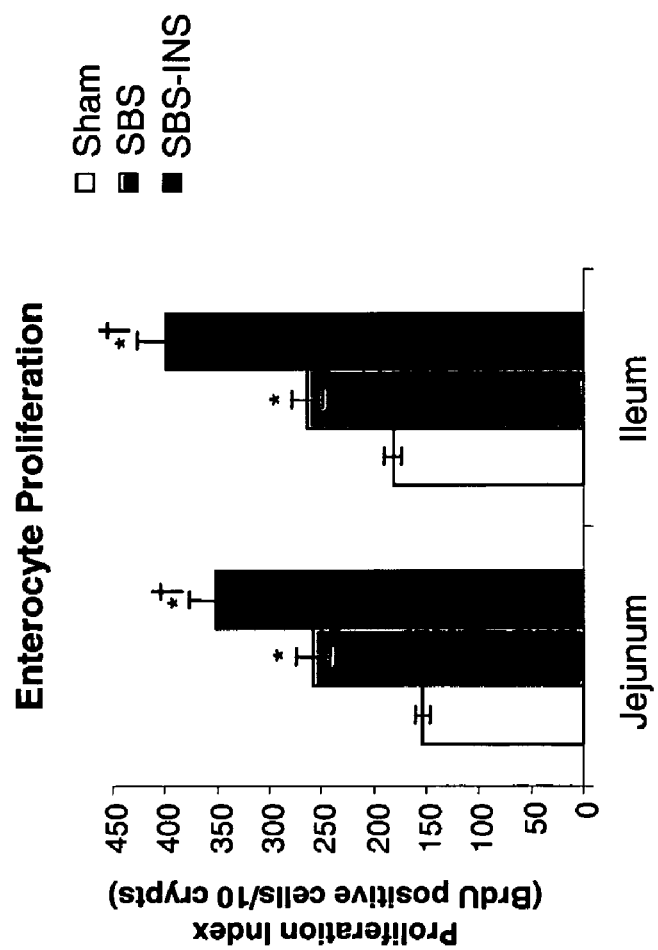

Oral insulin resulted in decreased enterocyte apoptosis in jejunum (see FIG. 2b). Both increased cell proliferation and reduced cell apoptosis may be responsible for increased enterocytes mass in jejunum during adaptation. In remaining ileum, oral insulin administration led to much more significant increase in enterocyte proliferation compared to jejunum without change in enterocyte apoptosis. Increased enterocyte proliferation rather than apoptosis is responsible for the bulk of enterocyte mass in remaining ileum.

In summary, oral insulin supplementation caused dramatic adaptive gut growth in a rat model of short bowel syndrome. Most significant changes were observed in remaining ileum.

Example 2

Oral Insulin Supplementation in Infants with SBS

In view of the successful results obtained in the rat model of SBS (Example 1, above), oral administration of insulin was effected in human subjects suffering from SBS.

Experimental Procedures

Inclusion Criteria:

1. Infants with less than 30 cm of small intestine (with ileo-cecal valve intact).

2. Infants with less than 40 cm without ileo-cecal valve.

3. Infants and children younger than 10 years of age, with SBS who are parrectal-enteral nutrition dependent and are not expected to be weaned of parrectal-enteral nutrition Exclusion criteria: Infants in an unstable condition such as sepsis, acute gastroenteritis, pneumonia.

Dosage: 1 unit of insulin (Actrapid, Novonordisk, Denmark)/kg body weight per dose×4/day (every 6 hours) was administered for 28 days. Insulin was administered every six hours. Insulin will be provided as 1 u/ml of 0.45 NaCl orally.

Glucose monitoring: Following the first insulin dose, blood glucose levels were measured, immediately prior to the first and second meal following the first dose of insulin. Measurements were repeated for the first three days following supplementation and then weekly (days 7, 14, 21 and 28)

Clinical Evaluation:

The clinical evaluation of the patients' conditions included the following parameters:

1. Weight, length, head circumference, MAC (mid arm circumference), TSF (triceps skin fold)—weekly 2. Growth rate 3. Rectal-enteral and parrectal-enteral intake of calories, carbohydrates, lipids 4. Blood concentration levels of glucose, albumin, ALT, AST, GGT, ALP, total cholesterol, triglycerides (fasting), HDL-cholesterol, insulin (fasting, before insulin administration)

5. Blood amino acid levels

6. Insulin antibodies. 1 ml of serum was removed prior to treatment and at day 28 following treatment. The samples were frozen at −70° C. and sent, on dry ice, to Division of Pediatric Gastroenterology and Nutrition, Meyer Children's Hospital of Haifa, Bat-Galim 31096, Haifa for analysis.

Results

Patient history: Male, Full Term, AGA, birth weight 3700 grams, suffered from malrotation and volvulus at 2 days of age. On laparotomy, severe ischemia was observed in the gut. Following 24 hours, another laparotomy was performed with 10 cm of proximal jejunum and 10 cm of terminal ileum recovered. An additional re-laparotomy was performed following a further 48 hours where most of the bowel was recovered, but 15 cm of terminal ileum was found to be necrotic. Partial small bowel resection and ileostomy were performed. The infant developed cholestatic jaundice post-surgery, with non-functional ileostomy and intestinal obstruction. An additional re-laparotomy was performed and 70% of the small bowel was found to be sick, necessitating massive bowel resection with 35 cm of terminal ileum and 10 cm of proximal jejunum preserved. One week later, yet another re-laparotomy was performed for recurrent intestinal obstruction with resection of 10 cm of structured bowel. When fully on parenteral nutrition and with severe cholestatic jaundice, oral insulin was started at the age of 3 months. Stool output, a decrease in jaundice, an increase in oral feeds and a reduced need for parenteral nutrition were observed within a few days after the initiation of treatment. Two months following the addition of oral insulin, parenteral nutrition was stopped and three months following the addition of insulin, the child was discharged from hospital, thriving and on full oral feeds.

Example 3

Effects of Oral Insulin on Intestinal Recovery Following Ischemia-Reperfusion Injury in Rat The purpose of the present study was to evaluate the effect of oral insulin supplementation on structural mucosal changes in the small bowel induced by ischemia and reperfusion (IR) injury in rats and to evaluate the mechanisms by which insulin might influences intestinal recovery including its effect on enterocyte proliferation and death via apoptosis.

Methods

Animals: Animals were obtained from the Rappaport Faculty of Medicine (Technion, Haifa, Israel). Male rats weighing 240-260 g were kept in individual stainless steel cages at constant temperature and humidity, and a 12-hour light-dark cycle was maintained. Rats were fasted 12 hours prior to the experiment with free access to water.

Experimental Design Thirty rats were randomly assigned to one of three groups: Group A—sham-rats underwent laparotomy (sham, n=10); Group B—IR-animals underwent occlusion of superior mesenteric artery and portal vein for 30 minutes followed by 24 hours of reperfusion (IR, n=10); Group C—IR-INS animals were pretreated with insulin given in drinking water (2%) for 3 days prior to and 24 hours following IR event (IR-INS, n=10).

Surgical procedure: Following overnight fasting, the animals were anesthetized with intraperitoneal injection of pentobarbital (IP 40 mg/kg). Using sterile techniques, the abdomen was opened using a midline incision. Sham underwent laparotomy and mobilization of superior mesenteric artery (SMA) and portal vein without their clamping. IR underwent laparotomy, mobilization and occlusion of SMA and portal vein by vascular clamp for 30 minutes followed by a reperfusion period of 24 hours. Before closure of the abdomen, the rats were resuscitated with a 3-ml intraperitoneal injection of warm 0.9% saline. For all operations, the abdominal cavity was closed in two layers with a running suture of Dexon "S" Polyglycolic Acid 3/0. Rats were allowed free access to water and food. Twenty-four hours later, the rats were anesthetized with intraperitoneal pentobarbital (75 mg/kg) and were sacrificed by open pneumothorax.

Intestinal Mucosal Parameters: The small intestine from the pylorus to the ileo-cecal valve was removed and divided into two segments: proximal jejunum and distal ileum. The intestine was split on the antimesenteric border, washed with cold saline, dried, and each segment was weighed. The mucosa was scraped from the underlying tissue with a glass slide and weighed. Bowel and mucosal weights were calculated as mg/cm bowel length/100 g body weight. Mucosal samples were homogenized with TRIzol reagent (Rhenium LTD, Jerusalem). DNA and protein were extracted by the method of Chomczynski [BioTechniques. 15:532, 1993] and were expressed as micrograms per centimeter of bowel per 100 g of body weight. In brief, 100 mg tissue was mixed with 1 ml of TRIzol reagent and homogenized for 2 min. Following a three minute incubation period and centrifugation the contents separated into three phases. DNA was isolated from the interphase using ethanol, washed with sodium citrate and was stabilised with 75% ethanol. Protein was isolated from the lower phase using isopropyl alcohol, washed with guanidine hydrochloride, and stabilised with 100% ethanol. Quantitation of DNA was performed with a spectrophotomer. Concentration of the final protein concentration was detected using Bio-Rad Protein Assay technique.

Intestinal Histology: Intestinal samples from the proximal jejunum and distal ileum were fixed in 10% formalin, dehydrated in progressive concentrations of ethanol, cleared in xylene, and embedded in paraffin wax. Deparaffinized 5 mm sections were stained with haematoxylin and eosin. Ten villi and crypts were selected for the microscopic analysis, using a 10×4 magnifying lens. Histological images were loaded on a 760×570 pixels resolution buffer using a computerized image analysis system composed of a trichip RGB video-camera (Sony, Japan), installed on a light microscope (Zeiss, Germany) and attached to an IBM compatible personal computer (Pentium III, MMX, 450 mhz, 125 MB RAM), equipped with a frame grabber. Images were captured, digitized and displayed on a high resolution color 17 inch monitor. The villus height and crypt depth were measured using the Image Pro Plus 4 image analysis software (Media Cybernetics, Baltimore, Md., USA).

The degree of intestinal tissue injury was evaluated on a grading scale from 0 to 8 as described previously by Park et al., [Surgery. 107: 574, 1990]: 0—normal mucosa, 1—subepithelial space at villus tip, 2—more extended subepithelial space, 3—epithelial lifting along villus sides, 4—denuded villi, 5—loss of villus tissue, 6—crypt layer infarction, 7—transmucosal infarction, 8—transmural infarction.

Enterocyte proliferation and apoptosis: Crypt cell proliferation was assessed using 5-bromodeoxyuridine (5-BrdU). Standard BrdU labeling reagent (Zymed Laboratories, Inc, San Francisco, Calif.) was injected intraperitoneally at a concentration of 1 ml/100 g body weight 2 hours prior to sacrifice. After paraffin removal, rehydration, and peroxidase inhibition, sections (5 μm) were successively incubated with a biotinylated monoclonal anti-BrdU antibody system provided in a kit form (Zymed Laboratories, Inc, San Francisco, Calif.). An index of proliferation was determined as the ratio of crypt cells staining positively for BrdU per 10 crypts.

Apoptotic cells were identified using the terminal deoxynucleotidyl transferase-mediated, dUTP nick end-labeling (TUNEL) assay. Terminal deoxynucleotidyl transferase (TdT) (Boehringer Mannheim GmbH, Mannheim, Germany) was used to label DNA strand breaks. Incorporation of fluorescein was detected by anti-fluorescein antibody Fab fragments from sheep, conjugated with horse-radish peroxidase (POD) (Boehringer Mannheim GmbH, Mannheim, Germany). Briefly, five-micrometer paraffin-embedded sections were dewaxed and rehydrated with xylene and graded alcohol. Tissue sections were microwave-pretreated in 10 mM citrate buffer (pH 6.0) and incubated with TUNEL reaction mixture containing nucleotide mixture with fluorescein-labeled deoxy-UTP and TdT at 37° C. for 60 min. Following incubation with blocking solution at room temperature for 30 minutes, the sections were incubated with Converted-POD at 37° C. for 30 minutes. TUNEL—positive color development was obtained by incubating the sections with AES substrate (Zymed Laboratories). The apoptotic index (AI) was defined as the number of apoptotic TUNEL-positive cells per 10 villi.

Statistical analysis: All data are given as mean±SD. Differences between experimental groups were tested for statistical significance (p<0.05) using the nonparametric Kruskal-Wallis ANOVA test, followed by the corrected Mann-Whitney test.

Results

Figure 4:
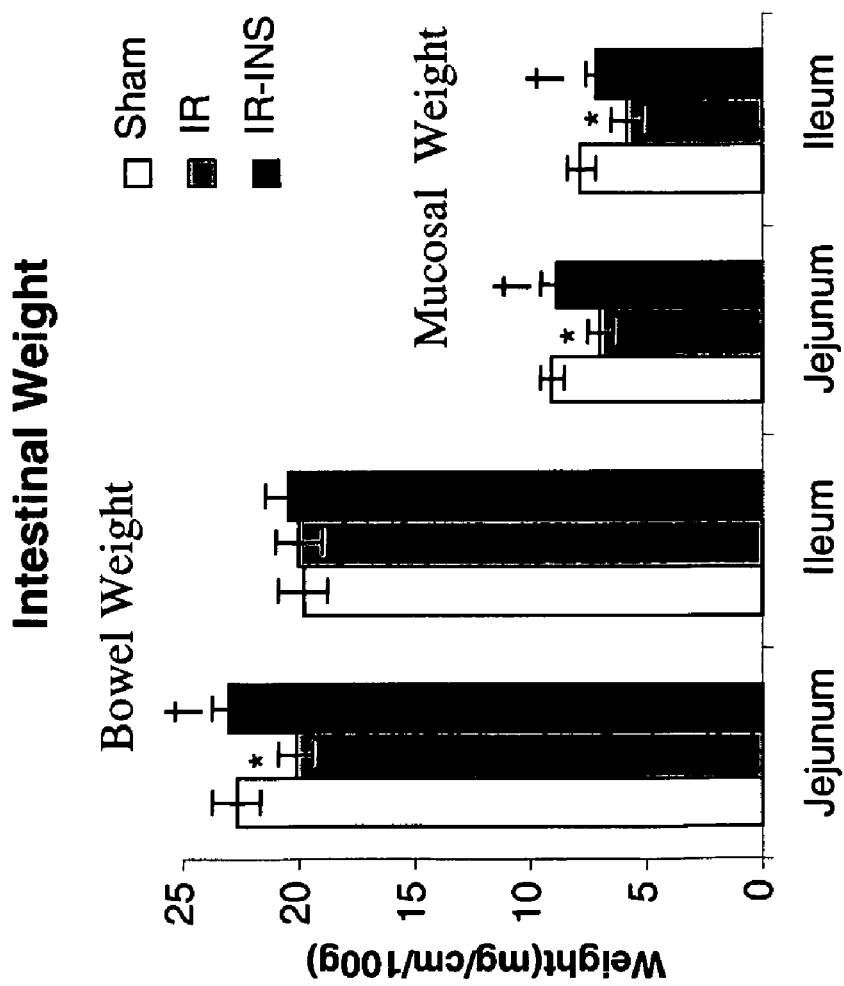
FIG. 4 is a graph depicting the effect of ischemia-reperfusion and oral insulin on the macroscopic intestinal appearance. Values are mean±SEM. IR—ischemia-reperfusion; INS—insulin, * P<0.05 IR vs Sham rats, † P<0.05 IR-INS vs IR rats.
Figure 5:
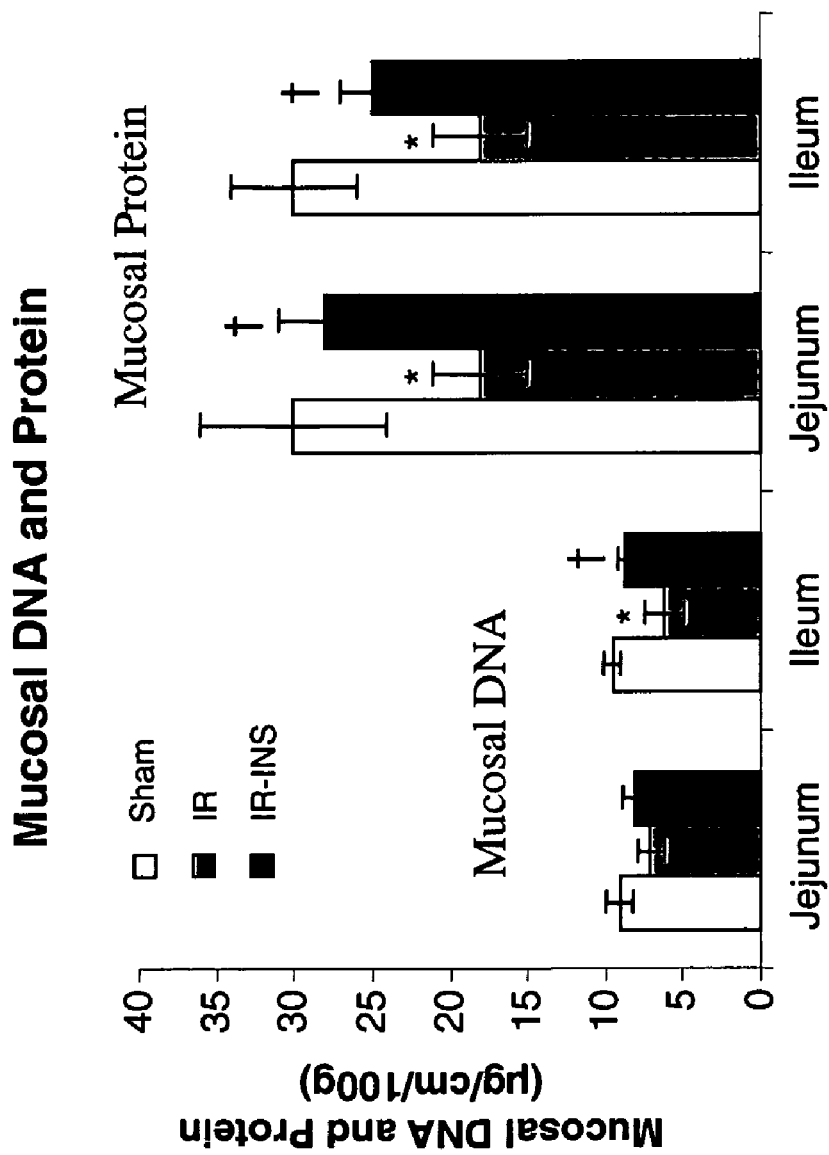
FIG. 5 is a graph depicting the effect of oral insulin on mucosal DNA and protein content following ischemia-reperfusion injury. Values are mean±SEM. IR—ischemia-reperfusion; INS—insulin. * P<0.05 IR vs Sham rats, † P<0.05 IR-INS vs IR rats.

Intestinal mucosal parameters: 80% of IR-animals and all sham animals survived the experimental protocol. There was no effect of oral insulin on post-operative mortality. IR rats (Group B) showed a significant decrease in bowel weight in jejunum (20.1±0.7 vs 22.7±1.0 mg/cm/100 g, p<0.05), mucosal weight in jejunum (7.0±0.6 vs 9.1±0.5 mg/cm/100 g, p<0.05) and ileum (5.9±0.6 vs 7.9±0.6 mg/cm/100 g, p<0.05) (FIG. 4), mucosal DNA in ileum (6.2±1.2 vs 9.6±0.5 mg/cm/100 g, p<0.05) (24.8±1.1 vs 30.7±2.7 μg/cm/100 g, p<0.05), mucosal protein in jejunum (18±3 vs 30±6 μg/cm/100 g, p<0.05) and ileum (18±3 vs 30±4 μg/cm/100 g, p<0.05) (FIG. 5) compared to sham animals (Group A). Administration of oral insulin (IR-INS, Group C) resulted in an increase in jejunal (23±0.8 vs 20.1±0.7 mg/cm/100 g, p<0.05) intestinal weight, jejunal (8.9±0.6 vs 7.0±0.6 mg/cm/100 g, p<0.05) and ileal (7.3±0.4 vs 5.9±0.6 mg/cm/100 g, p<0.05) mucosal weight (FIG. 4), mucosal DNA content in ileum (8.7±0.5 vs 6.2±1.1 mg/cm/100 g, p<0.05), mucosal protein in jejunum (28±3 vs 18±3 μg/cm/100 g, p<0.05) and ileum (25±2 vs 18±3 μg/cm/100 g, p<0.05) (FIG. 5) compared to IR animals (Group B) rats.

Figure 6:
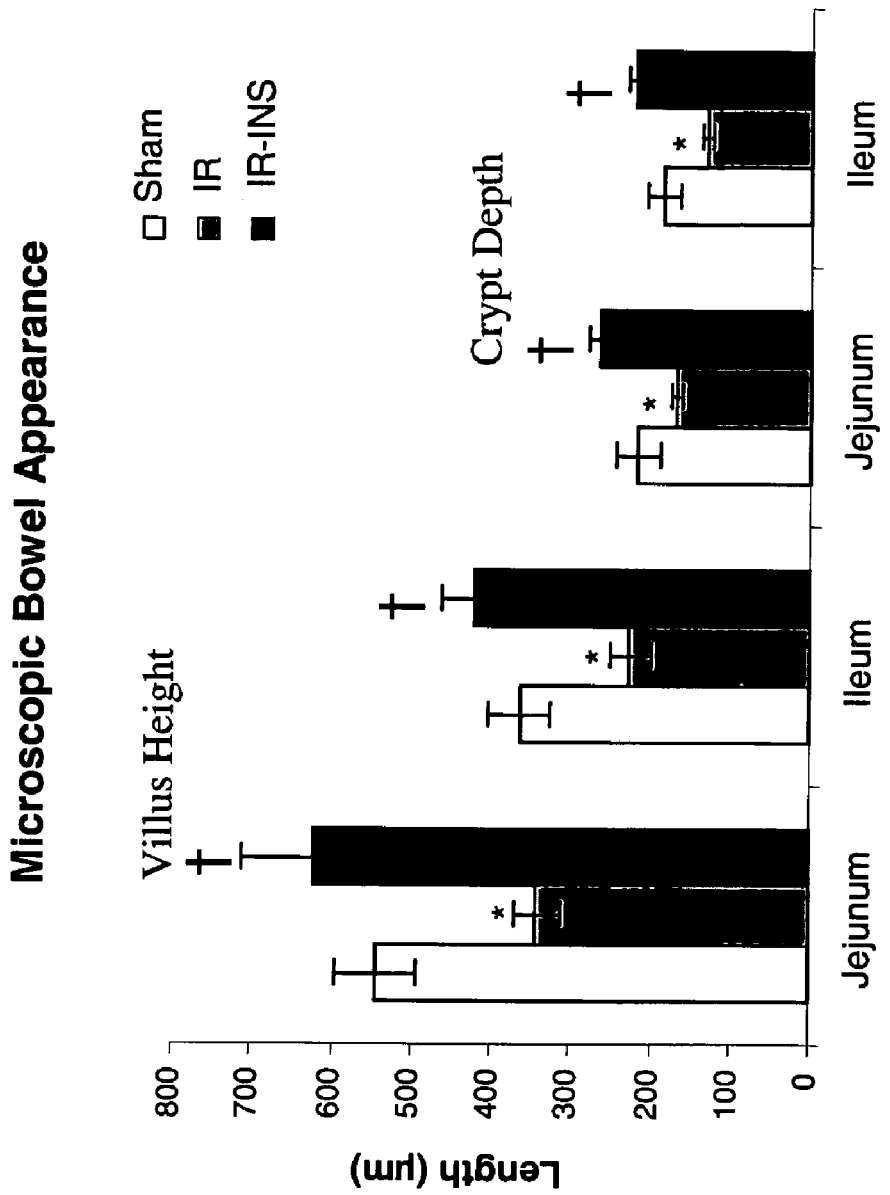
FIG. 6 is a graph depicting the effect of ischemia-reperfusion and oral insulin on the microscopic intestinal appearance. Values are mean±SEM. IR—ischemia-reperfusion; INS—insulin. * P<0.05 IR vs Sham rats, † P<0.05 IR-INS vs IR rats.

Microscopic bowel appearance IR rats exhibited a significant decrease in villus height in jejunum (341±29 vs 543±52 μm, p<0.05) and ileum (225±25 vs 363±39 μm, p<0.05), crypt depth in jejunum (167±8 vs 216±27 μm, p<0.05) and ileum (131±7 vs 184±21 μm, p<0.05) compared to sham animals (FIG. 6). Insulin treated rats (Group C) demonstrated a significant increase in jejunal (622±91 vs 341±29 μm, p<0.05) and ileal (421±40 vs 225±25 μm, p<0.05) villus height as well as in jejunal (264±13 vs 167±8 μm, p<0.05) and ileal (219±11 vs 131±7 μm, p<0.05) crypt depth compared to IR-animals (Group B).

Figure 7:
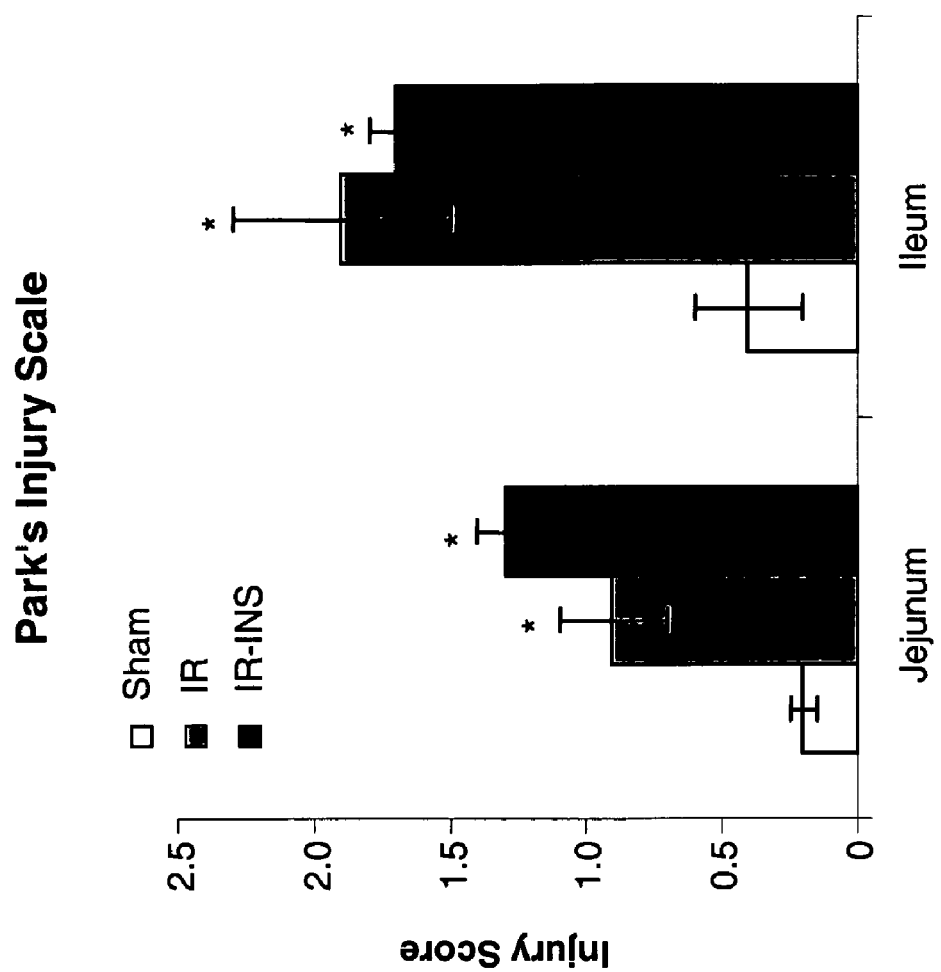
FIG. 7 is a graph depicting the grade of intestinal mucosal injury after intestinal ischemia-reperfusion and administration of oral insulin. Values are mean±SEM. IR—ischemia-reperfusion; INS—insulin. * P<0.05 IR vs Sham rats, † P<0.05 IR-INS vs IR rats.

IR injury (Group B) led to significant increase in the mean intestinal injury grade (Park's criteria) in jejunum and ileum compared to sham animals (FIG. 7). Oral insulin did not significantly change the injury grade in both jejunum and ileum compared to IR-animals.

Figure 8:
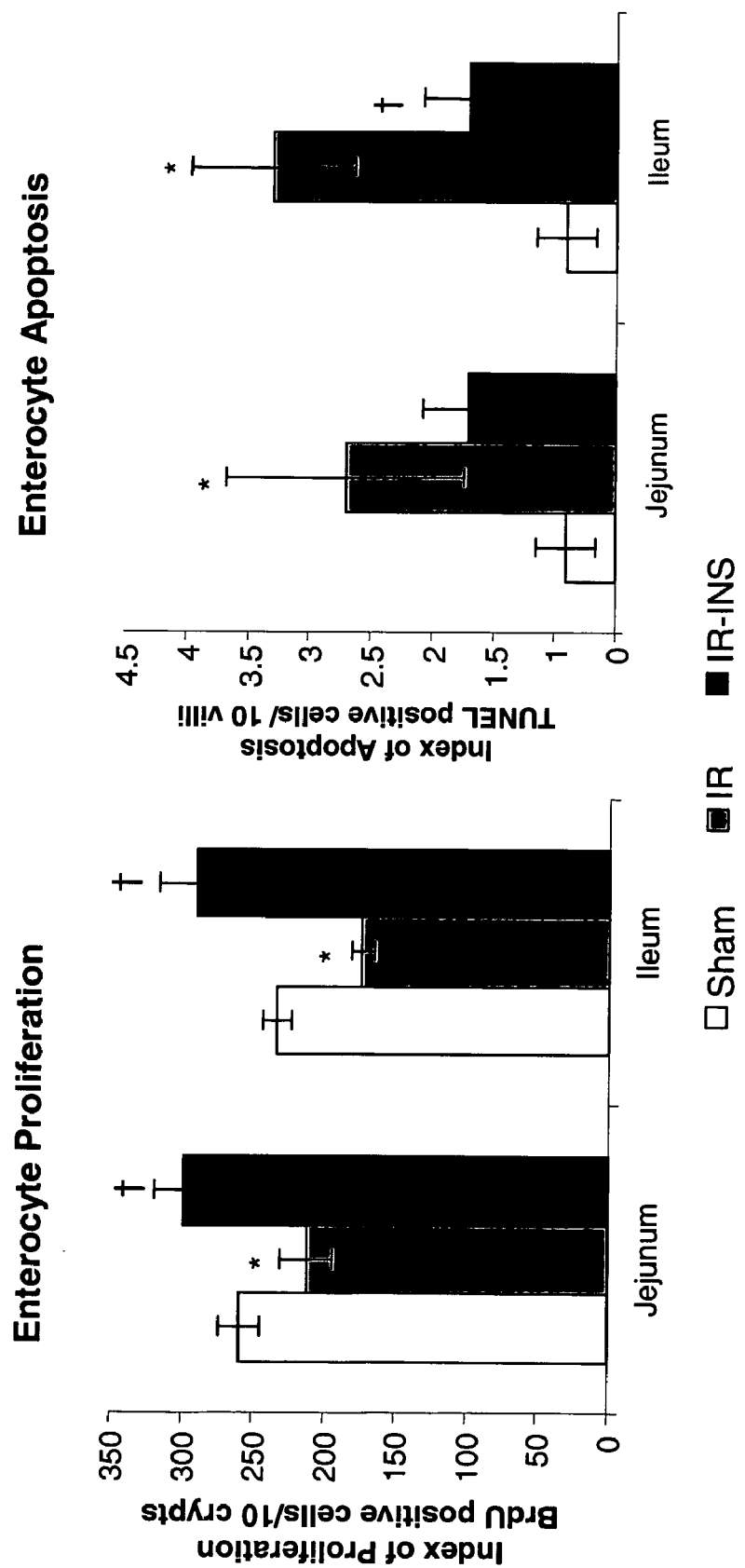
FIG. 8 is a graph depicting the effect of ischemia-reperfusion and oral insulin on crypt cell proliferation and enterocyte apoptosis in jejunum and ileum. 5-BrdU incorporation into proliferating jejunal and ileal crypt cells was detected with a goat anti-BrdU antibody, and TUNEL assay was used to determine enterocyte apoptosis. Values are mean±SEM. IR—ischemia-reperfusion; INS—insulin. * P<0.05 IR vs Sham rats, † P<0.05 IR-INS vs IR rats.

Enterocyte proliferation and apoptosis: IR rats (Group B) demonstrated a significant decrease in enterocyte proliferation index in jejunum (212±18 vs 252±16 BrdU positive cells/10 crypts, p<0.05) and ileum (173±8 vs 233±10 BrdU positive cells/10 crypts, p<0.05) compared to sham animals (FIG. 8). Oral insulin administration (Group C) induced a significant increase in enterocyte proliferation index in jejunum (298±21 vs 212±18 BrdU positive cells/10 crypts, p<0.05) and ileum (289±26 vs 173±8 BrdU positive cells/10 crypts, p<0.05) compared to IR animals (Group B) (FIGS. 9a-c).

Significantly greater numbers of apoptotic cells appeared in the villi of jejunum (2.2±1 vs 0.4±0.2 TUNEL positive cells/10 villi, p<0.05) and ileum (2.8±0.7 vs 0.4±0.2 TUNEL positive cells/10 villi, p<0.05) in IR rats (Group B) compared to sham animals (FIG. 8). Exposure to oral insulin led to significant decrease in apoptotic index in ileum (1.2±0.4 vs 2.8±0.7 TUNEL positive cells/10 villi, p<0.05) compared to IR-untreated animals (Group B).

Conclusion

Results show that IR caused a direct intestinal mucosal injury (as evident from increased Park's intestinal injury score) and lead to mucosal hypoplasia. The observed decreased bowel and mucosal weight, decreased mucosal DNA and protein, and decreased villus height and crypt depth in this model support this conclusion. Therefore, it should be emphasized, that mucosal hypoplasia rather than edema, vascular engorgement or intestinal muscle hypotrophy is responsible for the decreased intestinal mass after IR. Decrease enterocyte turnover, which is evident from decreased enterocyte proliferation and increased cell death via apoptosis, is responsible for this negative effect. Decreased villus height is presumably due to decreased cell proliferation and migration along villus axis or due to the specific arrangement of the villus microvasculature, which results in an oxygen tension gradient along the villus [Bohlen, H. G., 1980, Am J. Physiol. 238, H164, 1980].

Oral insulin produced various beneficial effects. Pretreatment with oral insulin did not protect the intestinal mucosa from damage caused by IR. IR-INS group manifested similar to IR-untreated animals intestinal mucosal injury grade, suggesting similar degrees of intestinal damage. However, exposure to oral insulin accelerated intestinal mucosal repair and enhanced enterocyte turnover. This is evident from the significant increase in bowel and mucosal weight, increased DNA and protein content, increased villus height and crypt depth in this model. Increased mucosal DNA and protein suggests accelerated cell metabolism, which is consistent with the enhanced epithelial cell proliferation. Histologically, marked increased villus height and crypt depth in both jejunum and ileum suggests expended absorptive surface area and closely correlate with large cell mass. The increase in cell proliferation of crypt cells increased significantly following oral insulin administration and closely correlated with increased crypt depth. Cell apoptosis rate decreased significantly in ileum of insulin treated rats, which may represent an additional mechanism that maintains mucosal integrity following IR.

In conclusion, administration of oral insulin did not prevent ischemic damage but accelerated intestinal recovery, enhanced enterocyte proliferation and decreased cell death via apoptosis following ischemia-reperfusion event It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Application

1. Coran A G, Spivak D, Teitelbaum D H (1999) An analysis of the morbidity and mortality of short bowel syndrome in the pediatric age group. Eur J Pediatr Surg 9: 228-230
2. Robinson M K, Ziegler T R, Wilmore D W (1999) Overview of intestinal adaptation and its stimulation. Eur J Pediatr Surg 9: 200-206
3. Sigalet D L, Martin G R (1998). Mechanisms underlying intestinal adaptation after massive intestinal resection in the rats. J Ped Surg 33: 889-892
4. Podolsky D K. Peptide growth factors in the gastrointestinal tract. In: Johnson L R, eds. Physiology of the gastrointestinal tract. Third edition. Raven Press, New York, 1994: 129-167
5. Laburthe M, Rouyer-Fessard C, Gammeltoft S. Receptors for insulin-like growth factors I and II in rat gastrointestinal epithelium. Am J Physiol 1988; 254: G457-G462
6. Lund P K. Molecular basis of intestinal adaptation: the role of the insulin-like growth factor system.
7. Lemmey A B, Martin A A, Read L C, Tomas F M, Owens P C, Ballard F J. IGF-I and the truncated analogue des-(1-3) IGF-I enhance growth in rats after gut resection. Am J. Physiol. 1991 February; 260(2 Pt 1):E213-9
8. Lemmey A B, Ballard F J, Martin A A, Tomas F M, Howarth G S, Read L C. Treatment with IGF-I peptides improves function of the remnant gut following small bowel resection in rats. Growth Factors. 1994; 10(4):243-52
9. Olanrewaju H, Patel L, Seidel E R. Trophic action of local intraileal infusion of insulin-like growth factor I: polyamine dependence. Am J Physiol 1992; 263: E282-286
10. Ziegler T R, Mantell M P, Chow J C, Rombeau J L, Smith R J. Gut adaptation and the insulin-like growth factor system: regulation by glutamine and IGF-1 administration. Am J Physiol 1996; 271: G866-G875
11. Lukish J, Yu D, Kato Y, Schwartz M Z. The effect of certain growth factors on intestinal function and adaptation following massive small bowel resection. Gastroenterology 1996; 110(Suppl): A818
12. Shulman R J. Oral insulin increases small intestinal mass and disaccharidase activity in the newborn miniature pig. Pediatr Res. 1990 August; 28(2):171-5
13. Shulman R J, Tivey D R, Sunitha I, Dudley M A, Henning S J. Effect of oral insulin on lactase activity, mRNA, and posttranscriptional processing in the newborn pig. J Pediatr Gastroenterol Nutr. 1992 February; 14(2):166-72
14. Shehadeh N, Wies R, Eishach 0, Berant M, Etzioni A, Shamir R. Influence of oral insulin supplementation on carbohydrate, lipid and protein metabolism in weaned Balb/c mice. J Pediatr Endocrinol Metab. 2003 16(3):431-7.
15. Shulman R J. Effect of rectal-enteral administration of insulin on intestinal development and feeding tolerance in preterm infants: a pilot study. Arch Dis Child Fetal Neonatal Ed. 2002 March; 86(2):F131-3.

What is claimed is:

1. A method of increasing intestinal function in the small intestine in a subject suffering from chemotherapy-associated intestinal malfunction, comprising orally administering to the subject a therapeutically effective amount of insulin, thereby increasing the intestinal function of said subject, wherein about 4 u/Kg body weight of said insulin is administered per day.

2. The method of claim 1, wherein said subject is a human subject.

3. The method of claim 2, wherein said human subject is an adult.

4. The method of claim 1, wherein said subject is a non-human mammal.

5. The method of claim 1, wherein said oral administration is effected by an oral dosage unit.

6. The method of claim 5, wherein said oral dosage unit is solid.

7. The method of claim 5, wherein said oral dosage unit is selected from the group consisting of a pill, a dragee, a tablet and a capsule.

* * * * *